US010265210B2

(12) United States Patent
Perez et al.

(10) Patent No.: US 10,265,210 B2
(45) Date of Patent: Apr. 23, 2019

(54) SCOLIOSIS BRACE

(71) Applicant: Aspen Medical Partners, LLC, Irvine, CA (US)

(72) Inventors: Joel Perez, Long Beach, CA (US); Geoffrey Garth, Long Beach, CA (US); Steven Burke, Huntington Beach, CA (US)

(73) Assignee: ASPEN MEDICAL PARTNERS, LLC, Irvine, CA (US)

( * ) Notice: Subject to any disclaimer, the term of this patent is extended or adjusted under 35 U.S.C. 154(b) by 117 days.

(21) Appl. No.: 14/504,244

(22) Filed: Oct. 1, 2014

(65) Prior Publication Data

US 2015/0018736 A1 Jan. 15, 2015

Related U.S. Application Data

(63) Continuation-in-part of application No. 13/888,117, filed on May 6, 2013.

(51) Int. Cl.
*A61F 5/02* (2006.01)

(52) U.S. Cl.
CPC .............. *A61F 5/026* (2013.01); *A61F 5/024* (2013.01)

(58) Field of Classification Search
CPC .. A61F 5/00; A61F 5/022; A61F 5/026; A61F 5/028; A61F 5/26; A61F 5/28; A61F 5/30; A61F 5/32; A61F 5/024; A61F 5/0193; A61F 5/01–5/0104; A61F 5/02–5/05; A61F 5/058; A61F 5/24–5/37; A61F 2005/0132–2005/0183; A61F 2005/0188; A61F 5/03;

(Continued)

(56) References Cited

U.S. PATENT DOCUMENTS

| 492,903 A | 3/1893 | Gerlitz |
| 1,257,297 A * | 2/1918 | Brown ................. A61F 5/0123 602/16 |
| 1,931,990 A | 10/1933 | Massek |

(Continued)

FOREIGN PATENT DOCUMENTS

| CA | 2175469 C | 6/1995 |
| DE | 19850993 A1 | 4/1999 |

(Continued)

OTHER PUBLICATIONS http://www.scoliosisjournal.com—Figure; Figure 2, Example of a double major scoliosis treated with a Cheneau light brace, printed on Dec. 12, 2012 at 4:26 pm.

(Continued)

*Primary Examiner* — Victoria J Hicks
*Assistant Examiner* — Michelle J Lee
(74) *Attorney, Agent, or Firm* — Fish IP Law, LLP

(57) ABSTRACT

A brace comprises a belt and removably attachable vertical strut(s). Each vertical strut can comprise one or more of a strut(s), thoracic pad(s), hip pad(s), lumbar support pad(s), chest support pad(s), de-rotation pad(s), or any other component suitable to assist or restrict movement of a wearer's body, reduce or apply a force to a wearer's body, correct the shape of a wearer's body, reduce pain, or provide support to a wearer's body. It is contemplated that each component can be removable or adjustable from a vertical strut or belt.

29 Claims, 9 Drawing Sheets

(58) Field of Classification Search
CPC ... A61F 5/3792; A61H 3/00; A61H 2003/007;
B25J 9/0006
USPC ..... 128/95.1, 96.1, 98.1, 99.1, 100.1, 102.1,
128/112.1, 846, 869, 870, 873, 876;
602/5, 12, 19, 60, 75
See application file for complete search history.

(56) References Cited

U.S. PATENT DOCUMENTS

| | | | |
|---|---|---|---|
| 1,935,859 A | | 11/1933 | Putz |
| 2,187,323 A | | 1/1940 | Kelton et al. |
| 2,687,129 A | * | 8/1954 | Talkish ............... A61F 5/024 |
| | | | 602/19 |
| 2,760,486 A | * | 8/1956 | Ward ................... A61F 5/024 |
| | | | 602/19 |
| 2,808,050 A | * | 10/1957 | Ward ................... A61F 5/024 |
| | | | 602/19 |
| 3,945,376 A | | 3/1976 | Kuehnegger |
| 4,230,101 A | | 10/1980 | Gold |
| 4,285,336 A | | 8/1981 | Oebser |
| 4,691,696 A | | 9/1987 | Faran de los Gdos |
| 4,907,575 A | | 3/1990 | Satterthwaite |
| 4,976,257 A | * | 12/1990 | Akin ................... A61F 5/024 |
| | | | 602/19 |
| 5,012,798 A | | 5/1991 | Graf |
| 5,244,924 A | | 9/1993 | Meinert |
| 5,405,313 A | | 4/1995 | Albin |
| 5,449,338 A | | 9/1995 | Trudell |
| 5,462,518 A | | 10/1995 | Hatley |
| 5,503,621 A | | 4/1996 | Miller |
| 5,538,449 A | | 7/1996 | Schwenn |
| 5,599,286 A | | 2/1997 | Labelle |
| 5,599,287 A | * | 2/1997 | Beczak, Sr. ............ A61F 5/026 |
| | | | 128/105.1 |
| 5,632,724 A | | 5/1997 | Lerman |
| 6,190,343 B1 | * | 2/2001 | Heinz et al. .................. 602/19 |
| 6,436,065 B1 | | 8/2002 | Mitchell |
| 6,471,665 B1 | | 10/2002 | Milbourn |
| 6,605,052 B1 | | 8/2003 | Cool |
| 6,893,411 B1 | * | 5/2005 | Modglin ............... A61F 5/0193 |
| | | | 128/882 |
| 7,766,850 B2 | | 8/2010 | Simanovsky |
| 7,967,767 B2 | | 6/2011 | Ogilvie |
| 8,066,653 B2 | * | 11/2011 | Seon ................... A61F 5/0123 |
| | | | 602/19 |
| 8,409,122 B2 | * | 4/2013 | Cropper ................ A61F 5/024 |
| | | | 128/876 |
| 8,657,769 B2 | * | 2/2014 | Ingimundarson et al. ..... 602/19 |
| 8,795,213 B2 | | 8/2014 | Mills |
| 8,926,537 B2 | | 1/2015 | Ingimundarson et al. |
| 8,945,034 B2 | | 2/2015 | Ingimundarson et al. |
| 9,439,800 B2 | | 9/2016 | Ingimundarson et al. |
| 2005/0059917 A1 | * | 3/2005 | Garth ................... A61F 5/028 |
| | | | 602/19 |
| 2008/0262402 A1 | | 10/2008 | Ogilvie |
| 2011/0295170 A1 | | 12/2011 | Laranjeira Gomes |
| 2014/0058307 A1 | * | 2/2014 | Marshall ................. A61F 5/02 |
| | | | 602/19 |

FOREIGN PATENT DOCUMENTS

| | | |
|---|---|---|
| EP | 2457544 A1 | 5/2012 |
| GB | 2467974 A | 8/2010 |
| KR | 10-2010-0089953 | 8/2010 |
| KR | 101070973 B1 | 10/2011 |
| TW | M424137 U | 3/2012 |
| WO | 2006068459 A1 | 6/2006 |
| WO | 2010044796 A1 | 4/2010 |

OTHER PUBLICATIONS http:/fwww.scoliosisjournal.com—Figure; Figure 2, Example of a double major scoliosis treated with a Cheneau light brace, printed on Dec. 12, 2012 at 4:26 pm.

* cited by examiner

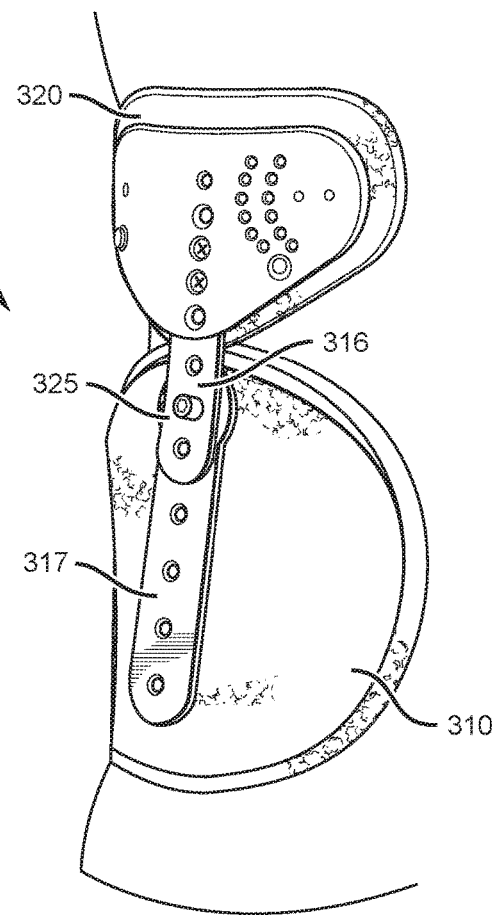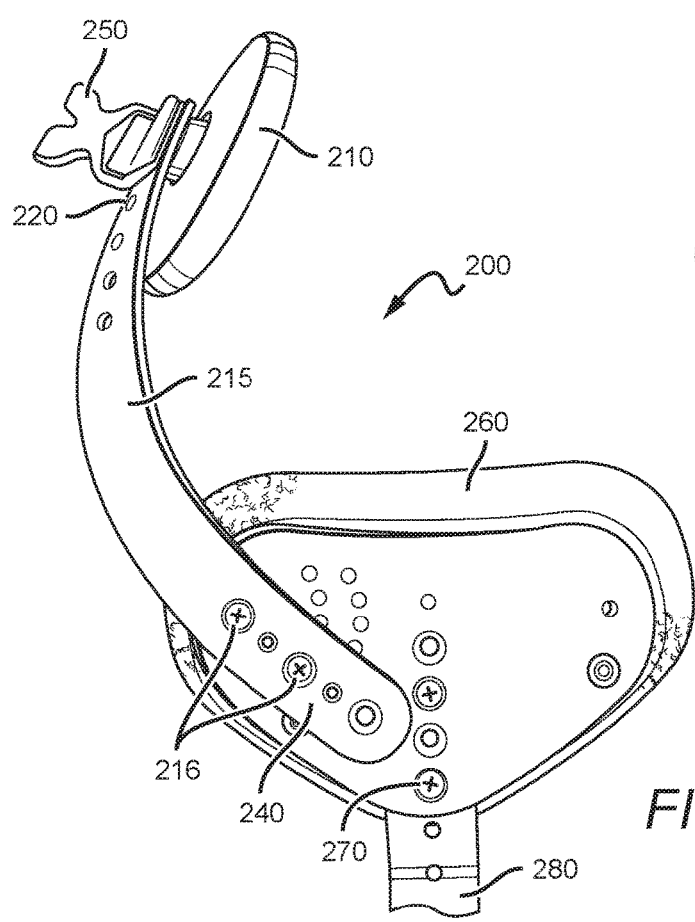

SCOLIOSIS BRACE

This application is a continuation-in-part of U.S. patent application Ser. No. 13/888,117, filed on May 6, 2013. All extrinsic materials identified herein are incorporated by reference in their entirety.

FIELD OF THE INVENTION

The field of the invention is orthotics.

BACKGROUND

The following description includes information that may be useful in understanding the present invention. It is not an admission that any of the information provided herein is prior art or relevant to the presently claimed invention, or that any publication specifically or implicitly referenced is prior art.

Scoliosis is a medical condition associated with an abnormally curved spine, often thought to be a progressive disease, at least until adulthood. Scoliosis can have severe adverse affects on a patient's life, both physically and physiologically. One possible method of treating or managing scoliosis is surgery. Unfortunately, scoliosis surgery can be very risky. Less invasive methods of treating or managing scoliosis has traditionally included physical therapy, chiropractic therapy, or bracing, among other things.

Some previous braces have been made to provide improved comfort, support, or customizability to individual wearers. For example, U.S. Pat. No. 4,230,101 to Gold, U.S. Pat. No. 5,012,798 to Graf et al., International Patent Application Publication No. WO 2010/044796 to Ogilvie et al., International Patent Application Publication No. WO 2006.068459 to Van Loon et al., U.S. Pat. No. 5,405,313 to Albin, and UK Patent Application GB 2467974 to Mills teach various scoliosis management devices.

All publications or other extrinsic evidence herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Unfortunately, none of the above references teach a brace that provides both the desired level of comfort, support and modularity to a wearer. Thus, there is still a need for improved scoliosis braces.

SUMMARY OF THE INVENTION

The inventive subject matter provides apparatus, systems and methods in which a scoliosis brace is configured to provide adjustable support to a wearer. The brace preferably comprises a flexible belt configured to wrap entirely around a mid-portion of a wearer, along with various components (e.g, struts, pads, adjustment mechanisms, etc.) configured to removably couple with the flexible belt and thereby provide customizable support to different portions of a wearer's body. A brace of the inventive subject matter can advantageously be configured to add a force or restrict a motion in the sagittal, transverse and coronal planes. By utilizing a belt wrapped around the mid-portion of the wearer, the belt can apply loading from the brace to middle targeted portion of the wearer, for example, a lateral side of the torso of the wearer.

One of the many advantages of a brace of the inventive subjective matter is that no strut is required on the front or back portions. Additionally, the lateral struts can often be covered or hidden beneath the arms of the wearer such that a passerby's attention is not immediately directed to the wearer's brace. Known scoliosis braces have at least one strut that is configured to contact the patient's dorsal and ventral surfaces. This is disadvantageous as these struts can cause extreme discomfort to the wearer (e.g., by pulling on the ribs or hips) and are aesthetically unappealing, making wearers self-conscious.

In one aspect of the inventive subject matter, a scoliosis brace comprises one or more vertical struts having an anchor pad (or base pad), and that is configured to removably couple to the belt, preferably on the belt's interior side of the belt (i.e., the side facing toward the wearer). It is contemplated that the anchor pad or the strut can removably attach to the belt in any commercially suitable manner, including for example, via a hook and loop fastener, snaps, buttons, magnets, and threading. The brace could include one or more vertical struts depending on the wearer's needs. Each of the struts could include one or more pieces without departing from the scope of the invention described herein. For example, the first strut could comprise two struts that are coupled together to form a single strut, or could instead comprise a unitary structure.

As used herein, a "vertical strut" is defined broadly to include a plurality of components (pads, struts, angle or height adjustment mechanisms, etc.) that are coupled with one another to create a single piece. A vertical strut can alternatively consist of a single component, for example, an anchor pad having a fastener to removably couple with a flexible belt of the inventive subject matter. As used herein, a "strut" is a single rod or bar forming a part of a framework. It can generally be preferred that a strut is made from either (1) a rigid material (e.g., a metal, a hard plastic, etc.) that requires more than an average person's force to bend, or (2) a material (e.g., aluminum, etc.) that is sized and dimensioned to be bendable when a strong force is applied. It is contemplated that a material that is bendable when a strong force is applied can additionally be sturdy enough not to deform when subjected to the loads inherent in its use and function.

In some embodiments, the first strut can include a thoracic pad at a first end portion such that the thoracic pad can provide a pressure to a first side of the wearer below the underarm. It is contemplated that the first strut can be composed of one or more pieces and could be configured to allow for adjustment of a height of the first strut to increase a distance between the belt and the thoracic pad. Where the first strut comprises two or more pieces, it is contemplated that the pieces could be movably coupled to one another such that one can rotate or pivot relative to the other.

A distance of the thoracic pad relative to the central point of the anchor pad can be adjusted via any commercially suitable height adjustment mechanism, including for example, a rack and pinion mechanism, a biasing mechanism, a slidably coupled telescoped component, or any other commercially suitable component. Similar mechanisms can also be provided to adjust a horizontal position of the thoracic pad relative to the central point of the anchor pad.

A brace of the inventive subject matter can also comprise a first hip pad coupled to the first strut, and configured to provide support to a hip area of a wearer. It is contemplated that the first strut could include a height adjustment mechanism (e.g., to adjust a vertical distance of the hip pad relative to the belt or an angle adjustment mechanism (e.g., to adjust a horizontal or vertical position of the hip pad on the wearer relative to the belt).

In another aspect of the inventive subject matter, it is contemplated that the thoracic pad can be coupled to a curved arm configured to at least partially wrap around an upper chest portion of a wearer. The curved arm is preferably coupled to a de-rotation pad that is configured to put pressure on the upper chest wall on one side to cause a force intended to resist forward motion and rotation of that side of the chest when the brace is worn.

One or more straps can be provided and configured to couple with two or more components of the brace. For example, a first strap can be coupled to the belt (e.g., via hook and loop fastener, snaps, buttons, threading, zipper, or other commercially suitable fastener(s) or combinations thereof) and the thoracic pad (e.g., via a carabiner, a buckle, a button, a snap, or other commercially suitable fastener(s) or combinations thereof). A second strap can be configured to couple to at least two of the following, among other components: the de-rotation pad, the rounded arm, the first strut, the anchor pad, or the hip pad.

In preferred embodiments, one or more vertical struts, anchor pads, struts, thoracic pads, de-rotation pads or hip pads can be coupled to the belt such that it provides support equally to a left or right side of the wearer. For example, where a belt is coupled with a right-side vertical strut but lacks a left-side vertical side, it is contemplated that the belt will provide an equal force to left side of a wearer's body to match the force applied to the right side of the wearer's body by the right-side vertical strut. Viewed from a different perspective, it is contemplated that a belt of the inventive subject matter can apply an equal pressure or force on opposing sides of the body regarding of the configurations of the struts and pads provided.

Viewed from another perspective, the inventive subject matter provides apparatuses, systems and methods in which a scoliosis brace includes a flexible belt configured to wrap entirely about a mid-portion, preferably between or about the waist and hip area, of a wearer. In some aspects, the flexible belt can include at least one of a fastener (e.g., a front-closure hook and loop fastener, etc.) and one or more systems that allows a user to adjust a tightness of the belt's fit on the wearer. Thus, the flexible belt can advantageously fit tightly around one or more vertical struts or anchor pads removably attached thereto, and substantially maintain a horizontal and vertical position thereof. As used herein, the term "substantially maintain" in connection with a "position" means that a position can be maintained within one inch of an original position when a brace is used for a two hour period.

Additionally, the flexible belt can at least partially determine a distribution of force that is applied to the right and left sides of a wearer via a brace of the inventive subject matter. For example, the first and second vertical struts could be coupled to the belt such that the first and second struts will be located at the wearer's right side and left side, respectively, when the brace is worn. The first vertical strut could include an anchor pad, a thoracic pad and a hip pad that are each sized and dimensioned to apply a pressure to the right side of the wearer. The second vertical strut could consist of an anchor pad sized and dimensioned to apply a pressure to the left side of the wearer. The belt could distribute the total force between the right side components and the left side components such that substantially the same pressure (i.e., within 10%) is applied to the right and left sides of the wearer, regardless of differences in the areas of the wearer's body to which each of the first and second vertical struts is applied. In this example, the sub-pressures applied to the right side of the wearer via the anchor pad, thoracic pad and hip pad can, in combination, substantially equal the pressure applied to the left side via the anchor pad. It should be appreciated that a length-wise distribution of the pressure applied by one vertical strut can be less than, greater than or substantially equal to a length-wise distribution of the pressure applied by a different vertical strut.

It is also contemplated that in some embodiments a belt of the inventive subject matter will distribute the total force such that the distribution of pressure applied to the right and left sides of the wearer corresponds to at least one of the surface area, length or width of the vertical struts that are applied to the different sides of the wearer.

One or more vertical struts can be removably coupled to the flexible belt at various positions that align with a wearer's body at different areas when the brace is worn. In some embodiments, a first vertical strut can be coupled to the belt at a position that aligns with the wearer's side (i.e., at least a portion of the vertical strut overlies the coronal plane of the wearer). Additionally or alternatively, the first vertical strut could comprise a top portion including a thoracic pad (or any other suitable pad), and a bottom portion including a hip pad (or any other suitable pad). The top portion can extend above the belt, and the bottom portion can extend below the belt such that at least portion of the pads are not confined under the belt when the brace is worn. Additionally or alternatively, a pad can couple to the belt such that the entire surface area of the pad is beneath the belt when worn by a user.

In some aspects of the inventive subject matter, a belt could substantially maintain a vertical position of one or more vertical struts relative to at least one of a wearer's mid-line and the belt's mid-line when the brace is worn. The vertical position of a vertical strut can include a vertical position of a top portion, a vertical position of a bottom portion or a vertical position of any other suitable components of the vertical strut. Additionally or alternatively, the belt could substantially maintain a horizontal position of the one or more vertical struts and its components.

In other aspects of the inventive subject matter, the one or more vertical struts of a brace could comprise a strut coupled to at least one of (1) a strut and a pad, and (2) a pad and a pad, and include or act as at least one of a height adjustment mechanism and an angle adjustment mechanism. A height adjustment mechanism can allow a user to adjust a distance between one or more components of a vertical strut (e.g., between a thoracic pad and an anchor pad or hip pad, etc.). An angle adjustment mechanism can allow a user to adjust an angle formed between a wearer's transverse or sagittal plane and a strut or other component.

In embodiments described herein where a second, third or even fourth vertical strut is provided, it is contemplated that the additional strut(s) can be positioned in any suitable manner to align with any desired portion of the wearer's body relative to the first vertical strut. For example, a second strut can be provided to predominantly support a side of the wearer opposite the first strut. The second strut can comprise or consist of, for example, a second anchor, a second thoracic pad, a second hip pad, one or more struts, or any combination thereof. The additional struts could further include a second de-rotation pad coupled to the second thoracic pad via a second rounded arm or any other suitable component(s).

Alternatively or additionally to being movably coupled to one another, each of the struts, straps, and pads can be removably coupled with, or attached to, another strut, pad, belt or other component of the inventive subject matter. Where a strut, pad or other component is moved from a first location to a second location, it is contemplated that the locations can be completely distinct or partially overlapping. For example, it is contemplated that a strut, pad or other component can be moved by as little as 5 cm, 2 cm, or even 1 cm or less, or can be moved by as much as 6 cm, 10 cm, or even 20 cm or even more.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 2 shows one embodiment of a thoracic pad, rounded arm and de-rotation pad of the inventive subject matter.

FIG. 3 shows one embodiment of another vertical strut of the inventive subject matter.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It is contemplated that a brace of the inventive subject matter can utilize one or more of the components discussed in co-owned U.S. Pat. Nos. 7,001,348 and 8,142,377, and U.S. Patent Application Publication Nos. 2012/0232450 and 2012/0245502. For example, it is contemplated that a brace can utilize a pulley system as disclosed in U.S. Pat. No. 7,001,348.

Figure 1:
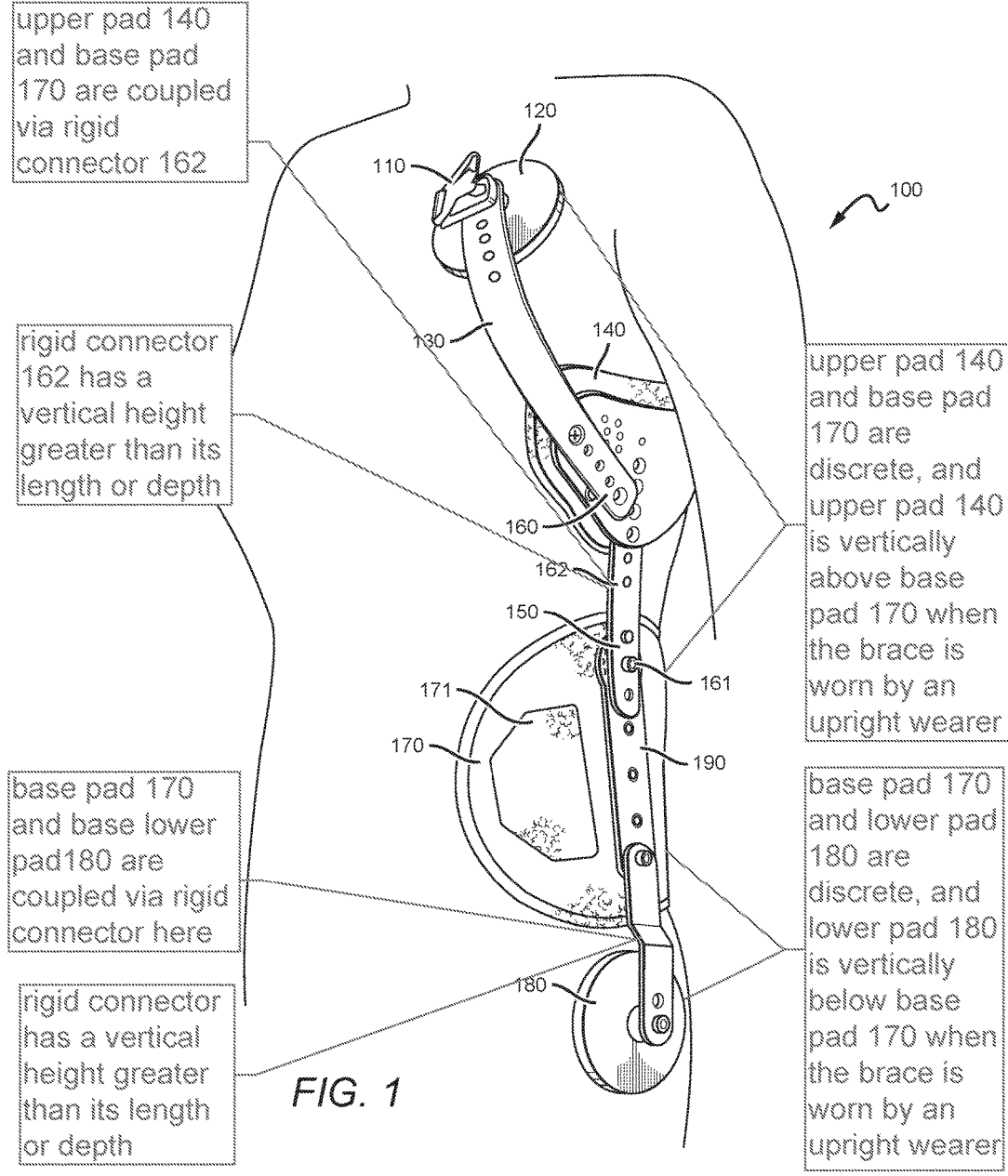
FIG. 1 shows one embodiment of a vertical strut of the inventive subject matter.

FIG. 1 shows a vertical strut 100 of the inventive subject matter. Vertical strut 100 is configured to provide support to a right or left side of a wearer, and preferably comprises an anchor pad 170 coupled with strut 190, a hip pad 180, and a thoracic pad 140. It is contemplated that a rounded arm 130 and a de-rotation pad 120 having a buckle receiver 110 can be coupled to the vertical strut depending on the needs of a wearer.

Anchor pad 170 comprises a hook or loop fastener 171 that is configured to removably attach to a belt (not shown). Contemplated pads can comprise any commercially suitable material(s), including for example, foam, silicon, nylon, cotton, mesh, or any other suitable material.

In some contemplated embodiments, strut 190 can be coupled to angle/height adjustment mechanism 150 that allows a user to adjust a horizontal or vertical location (i.e., a distance) of thoracic pad 140 relative to the anchor pad 170. One embodiment of such an angle/height adjustment mechanism is a second piece 162 that couples to the strut 190 via a screw mechanism 161. In such embodiments, the horizontal location of thoracic pad 140 relative to anchor pad 170 can be adjusted via adjustment mechanism 150 by simply rotating the second piece 162 relative to the first strut 190. The vertical height of thoracic pad 140 relative to anchor pad 170 can be adjusted via adjustment mechanism 150 by unscrewing screw 161, adjusting the alignment of perforations on the first strut 190 and second piece 162, and re-tightening screw 161.

First strut can thereby apply pressure above and below a wearer's mid-line via the upper thoracic pad 140 and lower hip pad 180, each of which is coupled to the first strut 190. By coupling the first strut 190 to a support belt that extends around a mid-portion of the wearer, the belt applies loading to each end of the first strut 190 and second piece 162 where used. In addition, the belt can preferably counteract a force applied to the left side of the wearer by vertical strut 100, regardless of whether or not the belt is coupled with one or more struts or pads that contact the right side of the wearer's body.

In other contemplated embodiments, other angle or height adjustment mechanisms can be used, including for example, a series of snaps, a rack and pinion mechanism, a biasing mechanism, a slidably coupled telescoped component, or any other commercially suitable mechanisms.

Optionally, a curved arm 130 can be coupled to second piece 162 or first strut 190, preferably via an angle/height adjustment mechanism 160. Curved arm 130 is coupled with de-rotation pad 120, which advantageously provides support to an upper chest region of a wearer, and is configured to at least partially prevent a rotation of a patient's torso when worn.

FIG. 2 is a close up view of a thoracic pad 260, curved arm 215 and de-rotation pad 210 of a vertical strut 200 of the inventive subject matter. Strut 280 is coupled to thoracic pad 260 via a fastener that can also act as a height adjustment mechanism 270. However, other types of fasteners could be used, and it is contemplated that strut 280 could lack a height adjustment mechanism. Thoracic pad 260 is further coupled to curved arm 215, which can also acts as a part of height and angle adjustment mechanism 240 in conjunction with one or more fasteners 216. It is contemplated that a user can remove or loosen fasteners 216 and realign the perforations of curved arm 215 with a suitable perforation of thoracic pad 260 in order to adjust an angle or height of de-rotation pad 210 relative to thoracic pad 260.

Although thoracic pad 260 is shown including a metal structure that holds padding in place, it is contemplated that the structure and thoracic pad could be distinct pieces coupled together to form thoracic pad 260.

De-rotation pad 210 can be coupled to curved arm 215 in any commercially suitable manner. However, it is currently preferred that de-rotation pad 210 and curved arm 215 are coupled together via a series of perforations and a snap configured to lock de-rotation pad 210 in a position aligned with one of the perforations.

De-rotation pad 210's fastener (height adjustment mechanism 220) is coupled to buckle receiver 250, which is configured to receive a buckle of a strap (not shown). A strap can be advantageously used to block a rotation of a component of the brace with respect to another component of the brace or providing a tension or tautness between the components to which it is attached. For example, a strap that is coupled to buckle receiver 250 and the belt can advantageously be used to block a change in a vertical position of a de-rotation pad relative to the belt, and further block a rotation of the vertical strut 200 comprising the de-rotation pad relative to the belt (alternatively or additionally to the blocking provided by a fastening mechanism between the belt and vertical strut).

FIG. 3 shows another embodiment of a vertical strut 300 of the inventive subject matter. Vertical strut 300 comprises an anchor pad 310, thoracic pad 320 and an optional adjustment mechanism 325 that allows for angular and height adjustment of the thoracic pad 320 relative to the anchor pad 310. The vertical strut can include first and second struts, 316 and 317, respectively, although a single strut could alternatively be used. It is contemplated that vertical strut 300 could also include additional components that are removable and adjustable with respect to the anchor pad 310 and thoracic pad 320. For example, vertical strut 300 could comprise a third strut coupled with a hip pad that extends below the anchor pad 310 in a direction opposite that of the thoracic pad. Alternatively or additionally, the hip pad could be coupled to a single strut that extends above and below the anchor pad.

It is contemplated that vertical strut 100 or 200 could be worn on a right side of a wearer while vertical strut 300 or 460 (below) is worn on a left side of a wearer, or vice versa. In such embodiments, loading can be applied to the left and right sides of the wearer simultaneously by coupling a vertical strut to the belt such that each strut aligns with an opposing side of the wearer.

Figure 4:
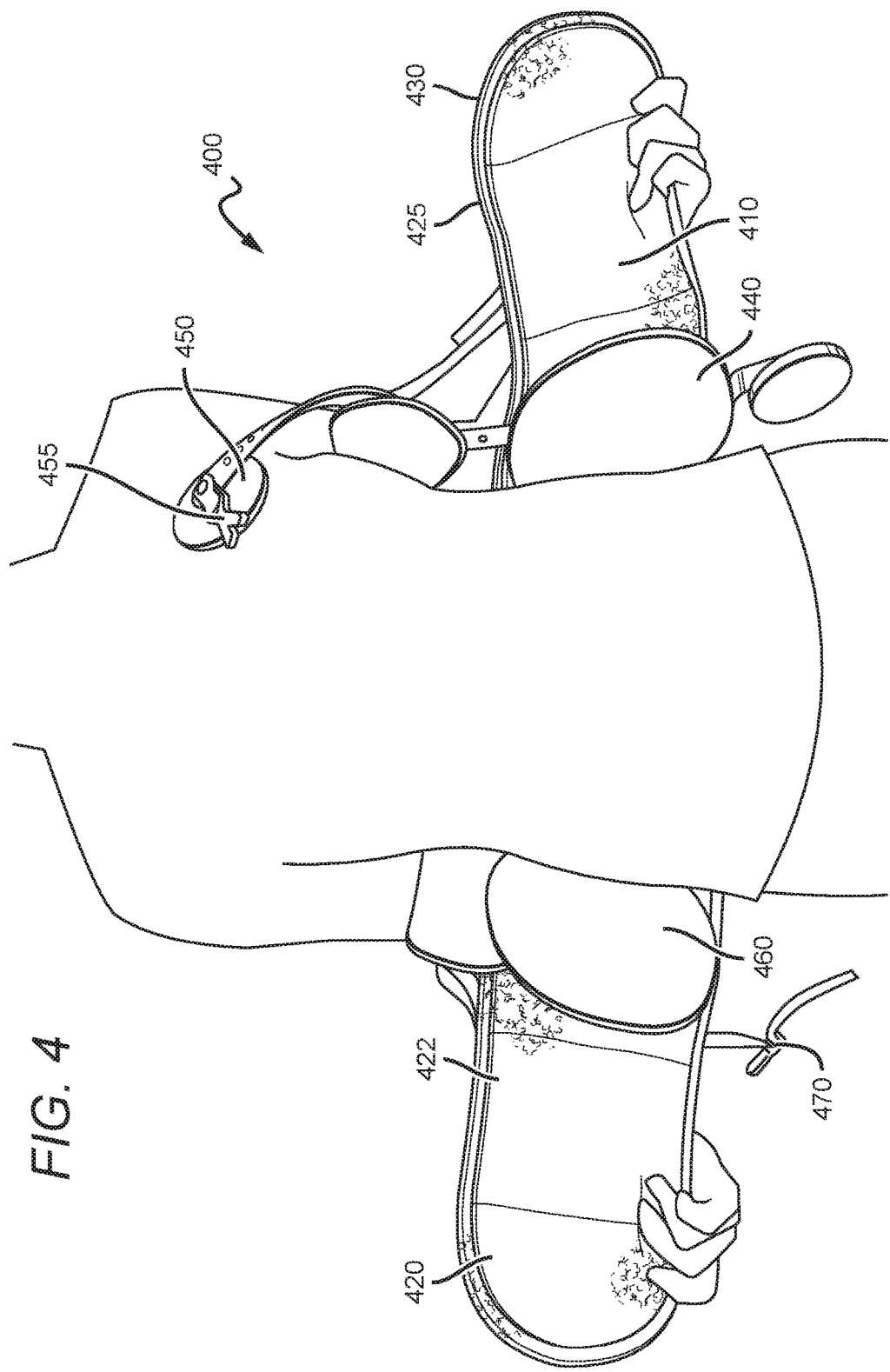
FIG. 4 shows one embodiment of a first and second vertical strut coupled to a flexible belt.

FIG. 4 shows a first vertical strut 440 and second vertical strut 460 each removably coupled to a belt 410 that wraps around a mid-line of the wearer. Belt 410 can include hook or loop fastener 420 on an inner side 422, and a complementary hook or loop fastener 430 on an outer side 425, which allows the belt to fasten to itself in some embodiments. Of course any commercially suitable fastener(s) could be used to couple the belt 410 to the wearer. Brace 400 also comprises a first vertical strut 440 removably attached to a left side of belt 400, and a second vertical strut 460 removably attached to a right side of belt 400. Preferably, each of the first and second vertical struts is coupled to an inner side of the belt—i.e., the surface of the belt facing towards the wearer when worn.

Belt 410 is preferably configured to wrap entirely around a mid-portion of a wearer and securely fasten to itself via hook or loop fasteners 420 and 430, although any commercially suitable fasteners could be used. In this manner, belt 410 can be used to support one or more vertical struts coupled to the belt. In some embodiments, the vertical struts can be coupled solely to the belt and thereby entirely be supported by the belt 410 disposed about a mid-portion of the wearer.

Depending on the wearer's needs, in some contemplated embodiments, brace 400 can include a first strap 470 coupled to the belt 410 at a first attachment point (on outer side 425), and configured to couple with a thoracic pad of second vertical strut 460, and de-rotation pad 450 of first vertical strut 440 via buckle receiver 455. First strap 470 and de-rotation pad 450 can be advantageously used together to cause an increase in pressure on a portion of the patient to support them in a desired position.

One having ordinary skill in the art should appreciate that references to a "fastener" are used broadly to refer to any commercially suitable fastener(s), including for example, a hook and loop fastener, a button, a snap, a belt type buckle, a side squeeze buckle, a magnet, a zipper, perforations and screws or snaps, or any other commercially suitable fastener(s). One having ordinary skill in the art should also appreciate that some fasteners can also serve as, or be coupled with, an adjustment mechanism such as a length, height, angle or other adjustment mechanism.

Figure 5:
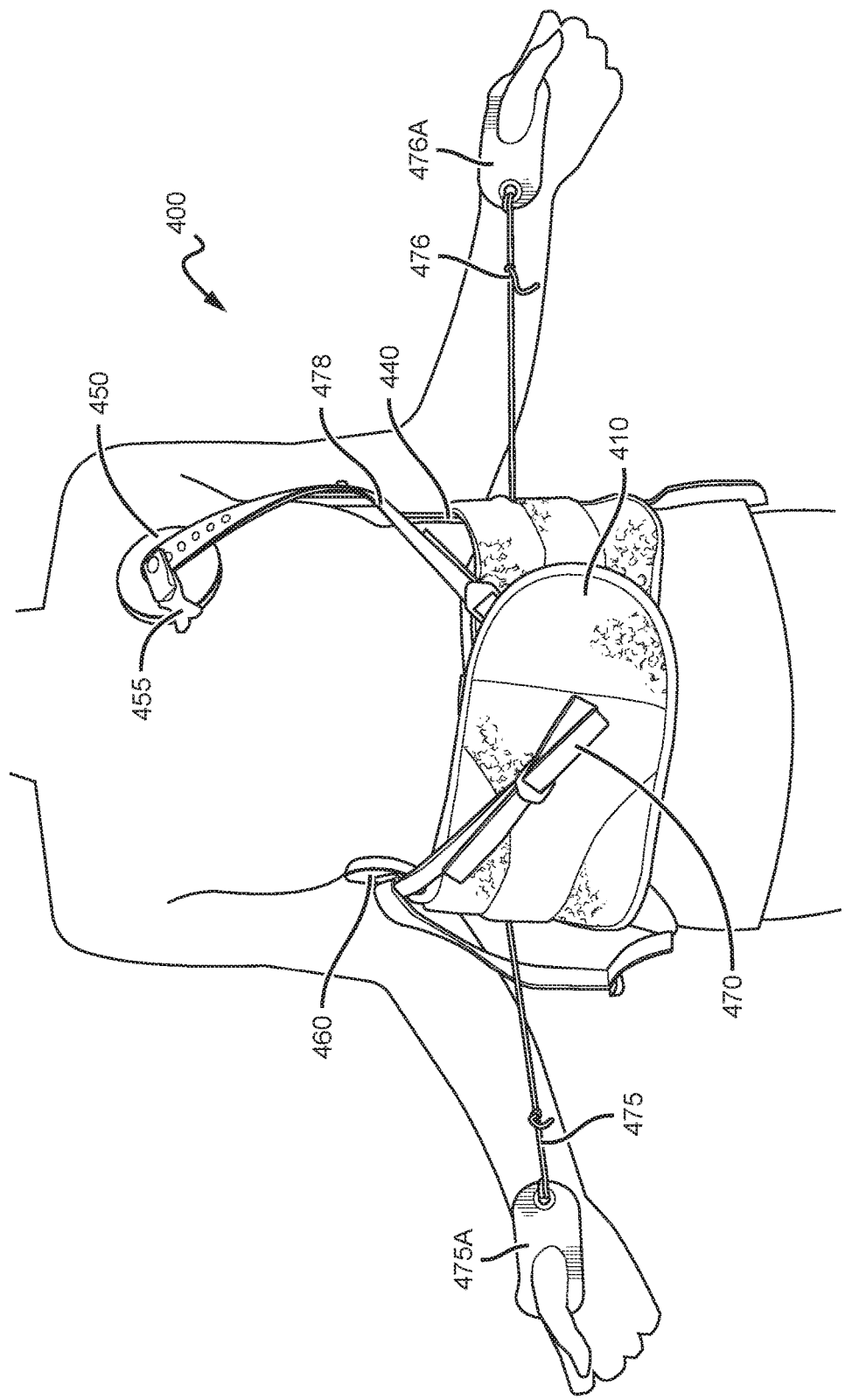
FIG. 5 shows one embodiment of a brace of the inventive subject matter as worn by a wearer.

FIG. 5 shows the brace 400 of FIG. 4 as partially fastened to a wearer. As shown, belt 410 is fastened to itself around the mid-portion of the wearer via hook and loop fasteners, and the brace 400 can be tightened via a first cord system 475 and a second cord system 476, although a single cord system could be used. It is contemplated that the pull tabs of cord systems 475 and 476 (e.g., 475A and 476A) can comprise a hook or loop fastener that can removably attach to a hook or loop fastener of the outer side of belt 400. As discussed above, it is contemplated that a brace of the inventive subject matter can utilize one or more of the components discussed in co-owned U.S. Pat. Nos. 7,001,348 and 8,142,377, and U.S. Patent Application Publication Nos. 2012/0232450 and 2012/0245502. For example, it is contemplated that a brace can utilize a pulley system as disclosed in U.S. Pat. No. 7,001,348.

Brace 400 can optionally comprise a second strap 478, which is fastened to an outer side of belt 400 via any suitable fastener (e.g., hook or loop, snaps, buttons, etc.) and further coupled to a thoracic pad of first vertical strut 440.

Figure 6:
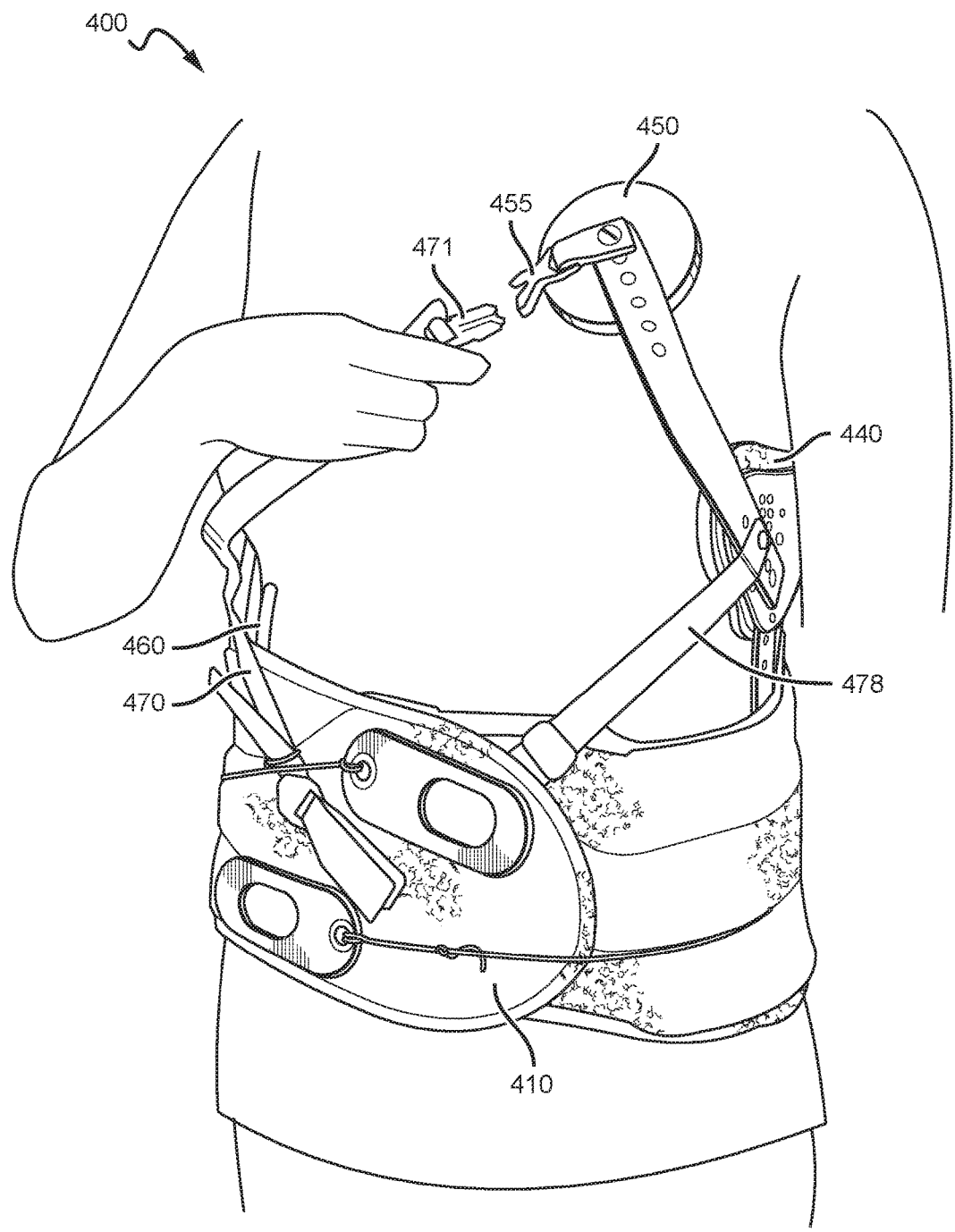
FIG. 6 shows one embodiment of a strap of the inventive subject matter having a buckle.

FIG. 6 shows a front-left side view of the brace 400 of FIGS. 4 and 5. First strap 470 is attached to belt 410 and second vertical strut 460, and is shown in being fastened to buckle receiver 455 of de-rotation pad 450 via buckle 471 of first strap 470. Second strap 478 is removably fastened to belt 410 and removably fastened to the thoracic pad of first vertical strut 440 via a screw that also acts as part of an angle and height adjustment mechanism between the curved arm and thoracic pad of first vertical strut 440.

Figure 7:
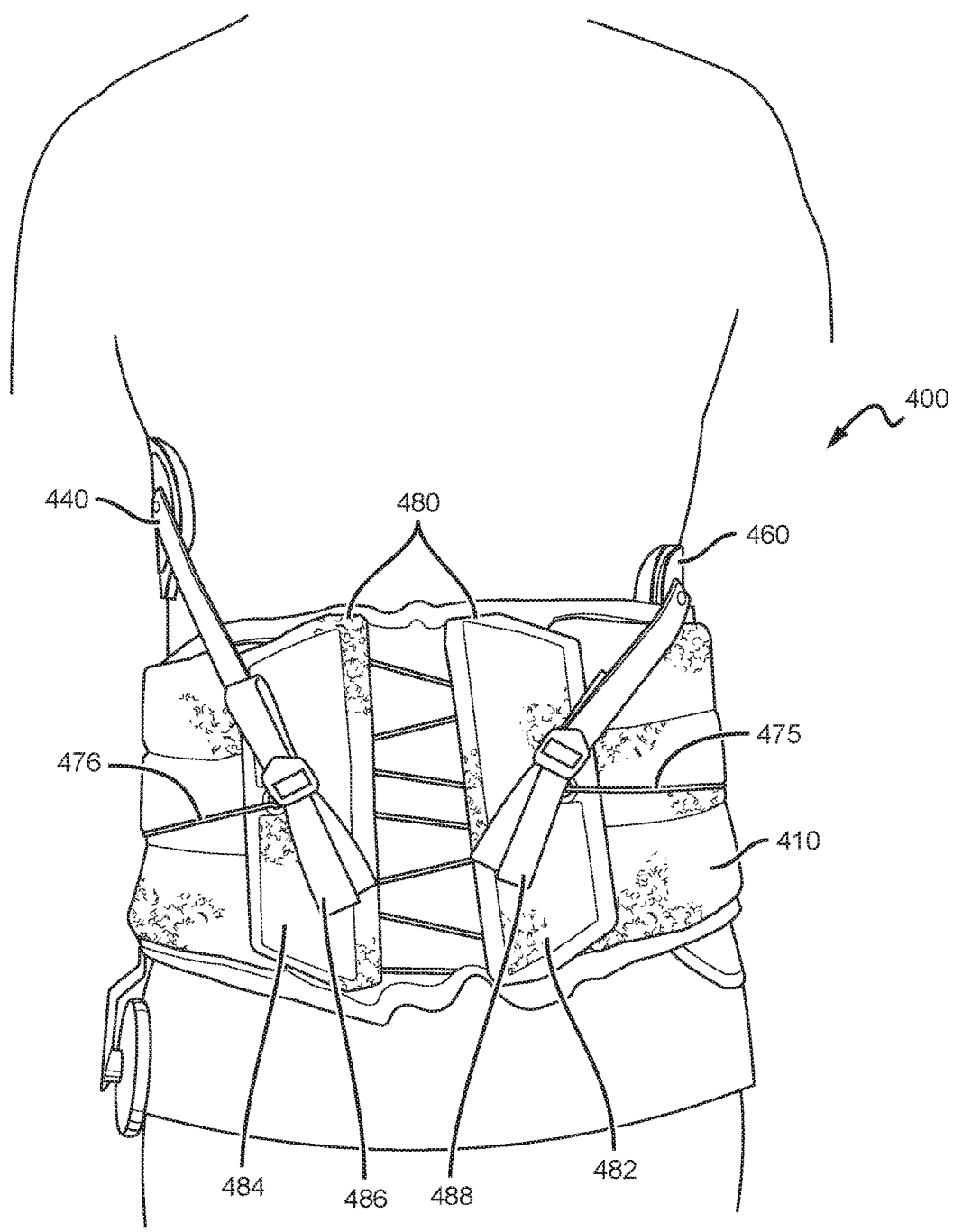
FIG. 7 shows one embodiment of a rear portion of a brace of the inventive subject matter.

FIG. 7 shows a back view of the brace 400 shown in FIG. 4 as worn by a wearer. Brace 400 comprises a tightening mechanism 480 shown in having two cord systems 475 and 476. It is contemplated that first cord system 475 can be configured to tighten a top portion of belt 410 (e.g., shorten a distance between the top portion of right cord guide cover 482 and left cord guide cover 484) when pulled in a first direction, while second cord system 476 can be configured to tighten a bottom portion of belt 410 (e.g., shorten a distance between the bottom portion of right cord guide cover 482 and left cord guide cover 484) when pulled in a second direction different from the first direction. Alternatively, each cord could be used to tighten a top and a bottom portion of belt 410.

Brace 400 further comprises a third strap 486 and fourth strap 488. Third strap 486 is configured to attach to left cord guide cover 484 and first vertical strut 440 via any suitable fastening means, and fourth strap 488 is configured to attach to right cord guide cover 482 and second vertical strut 460 via any suitable fastening means.

The combination of first, second, third and fourth straps (470, 478, 486, and 488) can be used together to provide increased support to a wearer while ensuring that a proper amount of force is being applied to the areas intended.

Figure 8:
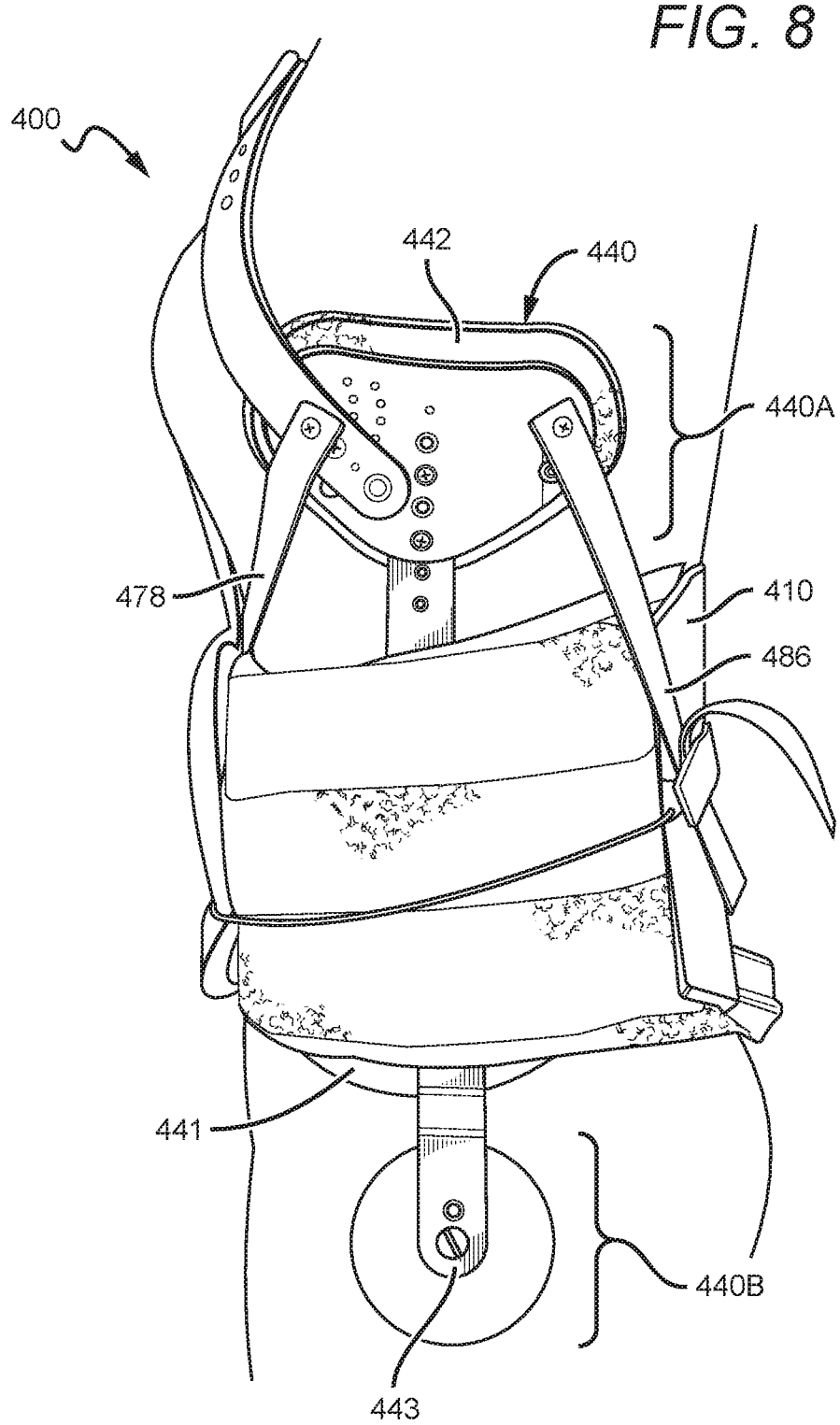
FIG. 8 shows one embodiment of a side portion of a brace of the inventive subject matter.

FIG. 8 is a left side view of the brace 400 of FIGS. 4-7 showing first vertical strut 440 coupled to an inner side of belt 410 that extends about a mid-portion of the wearer. As shown, anchor pad 441 is substantially aligned with the height of belt 410. Vertical strut 440 is configured to provide pressure to at least two portions of the wearer's body (e.g., upper and lower portions). The first area 440A (upper portion) is the left side of the wearer between the underarm and mid-portion, which is supported by thoracic pad 442. The second area (lower portion) 440B is the left hip of the wearer, which is supported by hip pad 443. In such embodiments, the vertical strut 440 is dependent on and supported by the belt 410, and loading is applied to the upper and lower portions of the wearer's body.

Optionally, second strap 478 and third strap 486 can each be fastened to belt 410 and thoracic pad 442, and are configured to provide an adjustable amount of tension or tautness between the two components to which they are attached, or prevent a rotation of one component (e.g., the thoracic pad 442) relative to another component (e.g., the midline of the belt where the belt could be folded in half along its length) to thereby prevent a rotation of a patient's body, or adjust the patient's body back into a less rotated state.

Figure 9:
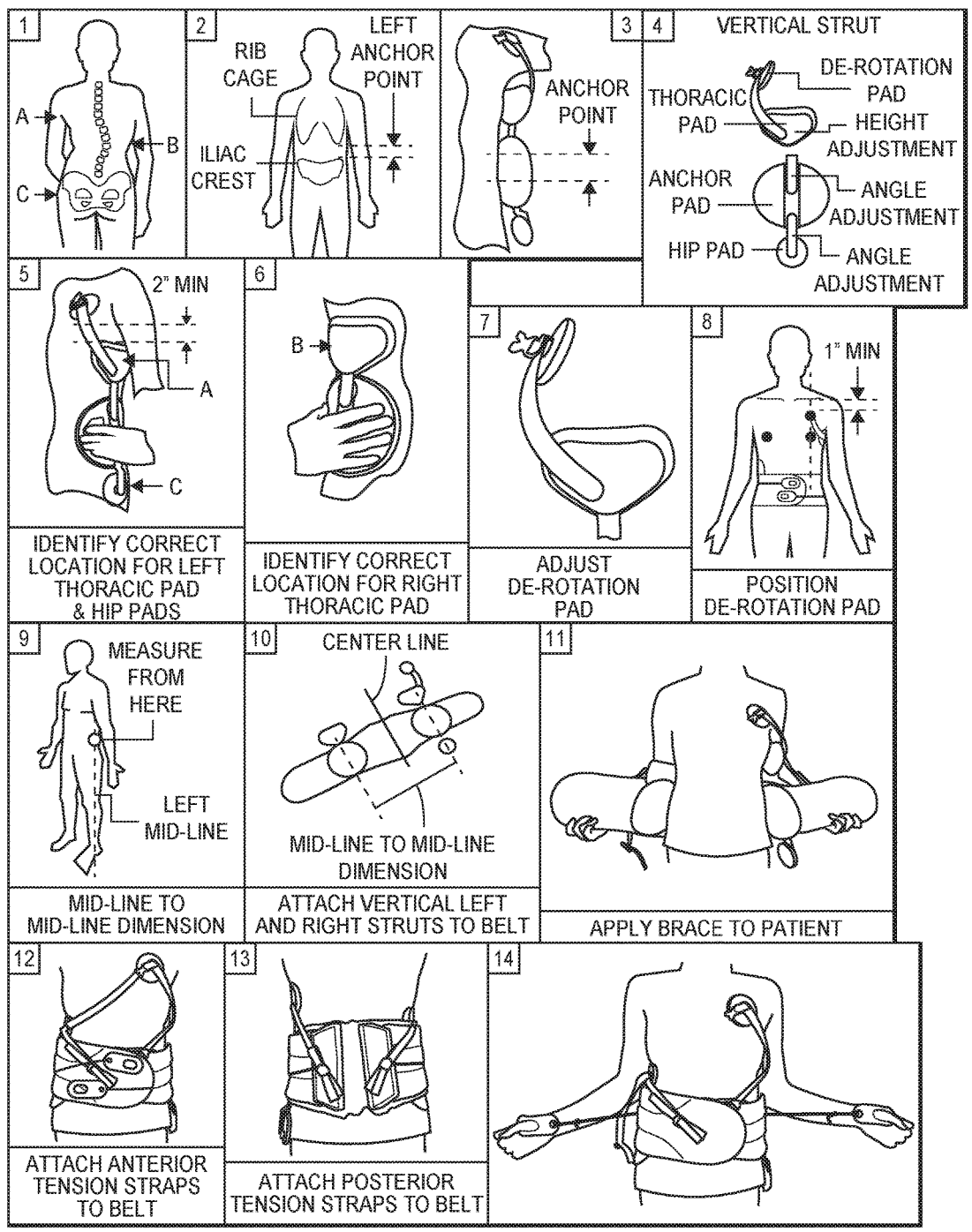
FIG. 9 shows a step by step flowchart of one method of fitting a wearer with a brace of the inventive subject matter.

FIG. 9 provides a step by step flowchart of one method of fitting a wearer with a brace.

As shown in step 1, a healthcare professional or other person can obtain an x-ray of a wearer's spine to identify a curve apex and locations where force should be applied. For example, step 1 shows that force should be applied at points A, B and C.

Step 2 shows how to locate an anchor point to which the anchor pad can be aligned (i.e., a mid-portion of the wearer). The left anchor point, for example, is located between the rib cage and iliac crest of the wearer. Depending on the curvature of the wearer's spine or other factors, it is contemplated that the anchor point(s) can alternatively be in a location other than between the rib cage and iliac crest.

Step 3 shows a vertical strut being fit on a wearer based on the anchor pad's alignment with the left anchor point. Once the location of the anchor pad is determined, the remaining components of the vertical strut can be adjusted (e.g., bending of the strut, adjustment of the relative heights of each component, adjustment of an angle between components, etc.) to provided a force to the intended areas of a user (e.g., areas A and C of step 1) as shown in Steps 4 and 5.

Step 4 shows a possible arrangement of components of a vertical strut, although some of the components may not be used. Step 5 shows that the thoracic pad of the first vertical strut can align with force point A. In this embodiment, it is generally preferred that at least two inches separate the underarm of the wearer and the top portion of the thoracic pad. In this embodiment, a Phillips screw driver can be used to align the thoracic and hip pads with previously identified locations where force will be applied.

Step 6 shows a second vertical strut being fit on the wearer based on a second anchor pad's alignment with the right anchor point. The thoracic pad of the second vertical strut is applied to force point B identified in step 1, which represents a curve apex of the wearer's spine on an opposite side of the wearer's body from force points A and C.

In step 7, a de-rotation pad can be optionally coupled to the first vertical strut and adjusted to fit the wearer. In this embodiment, the top edge of de-rotation pad is adjusted to be 1 inch below the clavicle of the wearer and directly above the nipple, as shown in Step 8. The de-rotation pad can be coupled to a curved arm or strut, which in this embodiment comprises bendable aluminum. This curved arm or strut can serve as an additional angle adjustment mechanism.

Once the first and second vertical struts have been adjusted to fit the wearer's body, a measurement can be taken between the wearer's left mid-line and the wearer's right mid-line as shown in Step 9.

Each of the first and second vertical struts can comprise a hook or loop fastener that is configured to removably fasten with a hook or loop fastener of either an inner or outer side of the belt (inner side shown here) as shown in Step 10. The center line of the belt should first be identified, and either strut should be attached on opposing sides of the center line such that a distance between the midlines of each anchor pad equals the distance between the left mid-line and the right mid-line previously measured in accordance with Step 9.

Step 11 shows a wearer putting on the brace after the first and second vertical struts have been fit and attached to the belt in accordance with Steps 1-10. The wearer aligns the anchor pads of each strut with the left or right anchor points and wraps the belt such that the ends of the belt overlap and fasten to one another. As shown in Step 12, the first ends of the first and second tension straps are then attached to the belt. A mid portion of the first tension strap is then attached to the second vertical struts thoracic pad, and a second end of the first tension strap is coupled with de-rotation pad via a buckle. The second end of the second tension strap is attached to the thoracic pad of the first vertical strut via a screw mechanism.

Step 13 shows third and fourth tension straps each attached to the belt and a different component of the brace. Step 14 shows the wearer tightening the brace through first and second cord systems that are pulled in opposite directions and fastened to the belt via pull tabs.

It is contemplated that a brace of the inventive subject matter can alternatively or additionally comprise other components, including for example, a lumbar pad, an underarm support, or a chest support pad.

Figure 10:
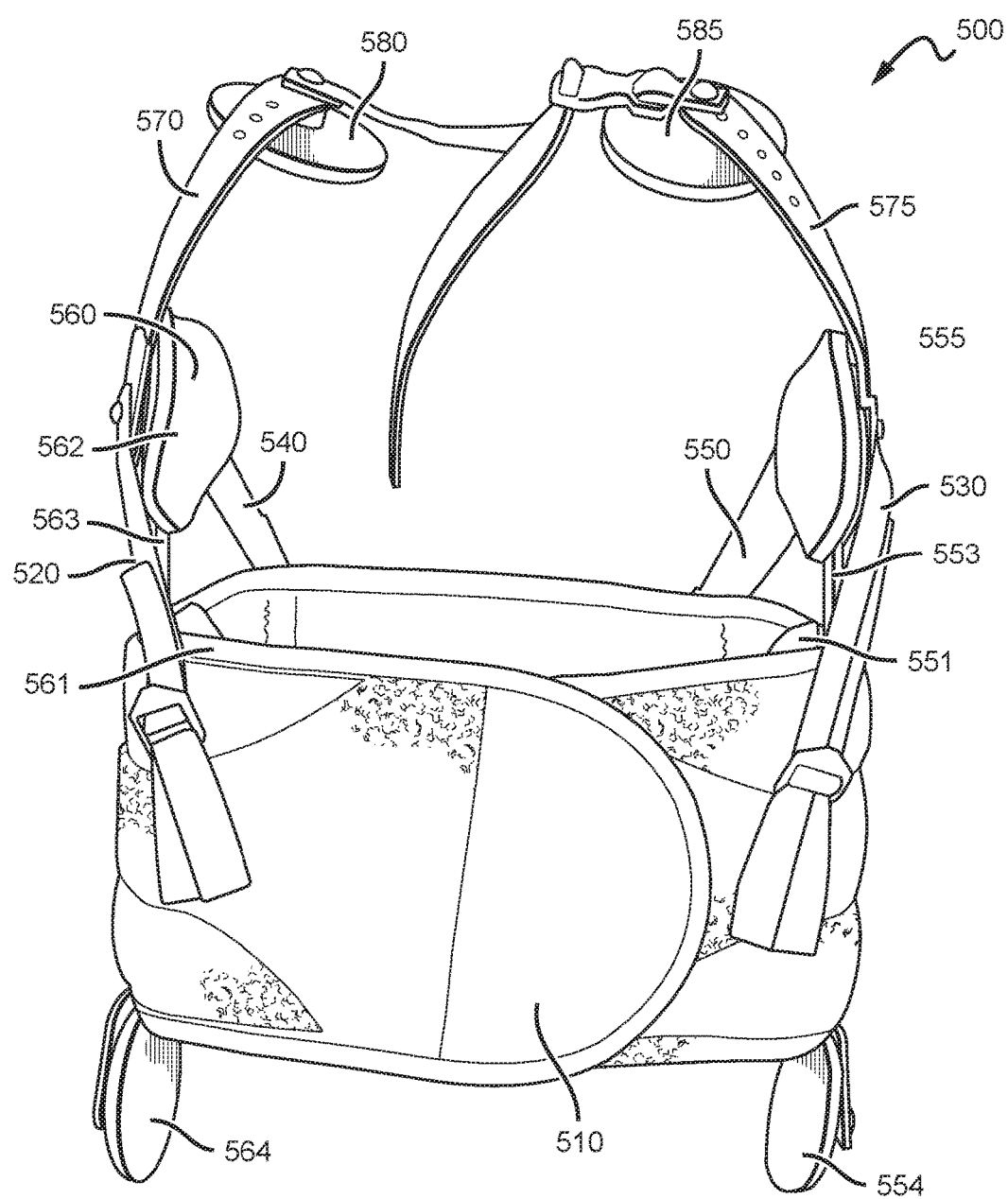
FIG. 10 shows another embodiment of a brace of the inventive subject matter having substantially similar left and right vertical struts with removable and adjustable components.

FIG. 10 shows another brace 500 of the inventive subject matter having substantially similar left and right vertical struts with removable and adjustable components. Brace 500 comprises a belt 510 that extends about a mid-portion of a wearer, and to which left and right vertical struts 555 and 560 can be coupled. The first vertical strut 555 comprises a first anchor pad 551, a first thoracic pad 552, and a first hip pad 554, all coupled to the first vertical strut. The second vertical strut 560 comprises a second anchor pad 561, a second thoracic pad 562, and a second hip pad 564, all coupled to the second vertical strut 560.

Optionally, the brace 500 can include a first tension strap 520, second tension strap 530, third tension strap 540, and a fourth tension strap 550.

In some embodiments, the first vertical strut 555 can include a second strut (e.g., 553) and a third strut, which are removably and adjustably coupled with first strut such that an angle or vertical position of the first thoracic pad and first hip pad can be adjusted relative to the first anchor pad, or even removed. Similarly, the second vertical strut 560 can include a fifth strut (e.g., 563) and a sixth strut, which are removably and adjustably coupled with third strut such that an angle or vertical position of the second thoracic pad and second hip pad can be adjusted.

Each of the first and second thoracic pads can optionally be coupled with a rounded arm, 570 and 575, which are in turn coupled with de-rotation pads, 580 and 585. The first and second straps can be removably attached to the front portion of belt 510 and a thoracic pad, while the third and fourth straps can be removably attached to the back portion of belt 510 and a thoracic pad. When the brace is worn, the tension straps can both block a rotation of a component of the brace relative to other components and provide increased tension or tautness between components of the brace.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A scoliosis brace for a wearer's body, comprising:
    a flexible belt configured to wrap entirely around a trunk portion of the wearer's body having an inner surface comprising a first hook or loop fastener;
    a first vertical strut comprising an upper pad, a lower pad, and a base pad having an outer surface portion that includes a second hook or loop fastener,
        wherein the first vertical strut can be removably attached to the inner surface of the belt via the first and second hook or loop fasteners at either a first position and removably attached to the inner surface of the belt via the first and second hook or loop fasteners at a second position different from the first position, and
        wherein the upper pad, the lower pad, and the base pad are discrete pads coupled by rigid connectors,
        the rigid connectors being sandwiched directly between the first hook or loop fastener and the second hook or loop fastener;
    wherein the brace is configured such that, when the brace is worn on the wearer's body when the wearer's body is upright:
        the upper pad is vertically above the base pad and the lower pad is vertically below the base pad,
        the upper pad applies a first force to a first side of a ribcage of the wearer's body from a first side of the wearer's body to a second side of the wearer's body along a coronal plane,
        the lower pad applies a second force to a first side of a hip of the wearer's body from the first side of the wearer's body to the second side of the wearer's body along the coronal plane, and
        the flexible belt applies a third force to the second side of the wearer's body between the ribcage and the iliac crest of the wearer's body opposite the first force and the second force, from the second side of the wearer's body to the first side of the wearer's body along the coronal plane.

2. The scoliosis brace of claim 1, further comprising at least one of a second base pad and a second vertical strut that can be removably coupled to the inner surface of the belt at a third position such that the belt applies the third force to the second side of the wearer's body through the at least one of the second base pad and the second vertical strut when the brace is worn.

3. The scoliosis brace of claim 2, wherein the belt substantially equates the first force and the second force with the third force when the brace is worn.

4. The scoliosis brace of claim 1, wherein a major face of the upper pad is configured to apply the first force to the ribcage of the wearer at least two inches below an underarm of the wearer, wherein the major face of the upper pad comprises a surface of the upper pad having a larger surface area than at least one other face of the upper pad.

5. The scoliosis brace of claim 4, wherein the major face of the upper pad is tilted upwards, and wherein the first force also comprises an upward force configured to be applied to an underside of the ribcage of the wearer's body from a foot of the wearer's body to a head of the wearer's body when the wearer's body is upright.

6. The scoliosis brace of claim 1, wherein a location of where the first vertical strut attaches to the inner surface of the belt is configured to at least partially determine a distribution of forces between the first force, the second force, and the third force.

7. The scoliosis brace of claim 1, wherein the base pad is configured to contact the wearer's body when the brace is worn, and wherein the brace is further configured to restrict a motion of the wearer's body along a sagittal plane and a transverse plane when the brace is worn.

8. The scoliosis brace of claim 1, wherein a length of the first vertical strut is adjustable between at least one of (a) the upper pad and the base pad, and (b) the lower pad and the base pad.

9. The scoliosis brace of claim 1, further comprising a first tension strap that extends from the first vertical strut to the flexible belt at a position anterior to the first vertical strut.

10. A scoliosis brace of claim 1, wherein the first side is the left or right side of the wearer's body, and wherein the base pad is configured to be positioned between the rib cage and the iliac crest of the wearer's body when the brace is worn.

11. The scoliosis brace of claim 1, wherein a rigid portion of the upper pad is sized and disposed to at least partially wrap around both an anterior portion and a posterior portion of the ribcage of the wearer.

12. The scoliosis brace of claim 1, wherein any rigid horizontal width of the first vertical strut between the base pad and the lower pad or the upper pad is less than at least one of any rigid horizontal width of the base pad and any rigid horizontal width of the lower pad or upper pad.

13. A customizable scoliosis brace, comprising:
a flexible belt adjustably wrappable around a trunk portion of a wearer's body, the flexible belt including a tightening system that allows a user to adjust a tightness of the belt on the wearer's body when the flexible belt is wrapped around the trunk portion;
a vertical strut comprising an upper pad, a lower pad and an anchor pad,
wherein the upper pad, lower pad, and anchor pad are discrete pads coupled by rigid connectors,
wherein the vertical strut is removably coupleable to an inner surface of the belt at more than one different location via a hook and loop fastener,
wherein the hook and loop fastener comprises a first hook or loop material on an outer portion of the anchor pad and a second hook or loop material on the inner surface of the belt,
the rigid connectors being sandwiched directly between the first hook or loop material and the second hook or loop material; and
wherein when the scoliosis brace is worn on an upright wearer:
the upper pad is vertically above the anchor pad and the lower pad is vertically below the anchor pad;
the upper pad is configured to be positioned above the belt and the lower pad is configured to be positioned below the belt at a hip of the wearer's body;
the upper and lower pads are configured to apply a first force to a left or right side of the wearer's body and to restrict a motion of the wearer's body along a coronal plane; and
the flexible belt is configured to apply a second force to a second side of the wearer's body opposite the first force; and
wherein the vertical strut is configured such that the vertical strut can be entirely supported by the flexible belt.

14. The scoliosis brace of claim 13, wherein the tightening system includes a first cord that sinuously engages cord guide lobes of first and second cord guides, and is configured to shorten a distance between first and second cord guides when pulled in a first direction.

15. The scoliosis brace of claim 14, wherein the tightening system further comprises a second cord, and wherein the tightening system can be used to tighten the belt by pulling the first cord in the first direction and pulling the second cord in a second direction opposite the first direction.

16. The scoliosis brace of claim 13, wherein the tightening system includes a pulley system.

17. The scoliosis brace of claim 13, wherein a height adjustment mechanism is configured to allow the user to adjust a distance between the upper pad and the anchor pad.

18. The scoliosis brace of claim 13, wherein the vertical strut further comprises an angle adjustment mechanism configured to allow the user to adjust an angle of the vertical strut between the first pad and the second pad, wherein the angle adjustment mechanism comprises a first strut piece and a second strut piece coupled to one another such that the first strut piece is configured to rotate relative to the second strut piece.

19. The scoliosis brace of claim 13, wherein when the brace is worn, the more than one different locations on the inner surface of the flexible belt are positioned on the left or right side of the wearer.

20. A scoliosis brace for a wearer, comprising:
a flexible belt configured to wrap entirely around a trunk portion of the wearer;
a first vertical strut including a base portion, a top portion and a bottom portion,
wherein the base portion, top portion, and bottom portion are discrete pads coupled by rigid connectors,
wherein the base portion is configured such that it can be removably attached to an inner surface of the flexible belt in two different places along a length of the flexible belt via a hook and loop fastener such that the top portion extends above the belt and the bottom portion extends below the belt,
wherein the hook and loop fastener comprises a first hook or loop material positioned on the inner surface of the flexible belt, and a second hook or loop material positioned on an outer surface of the base portion,
the rigid connectors being sandwiched directly between the first hook or loop material and the second hook or loop material; and
wherein when the brace is worn on the wearer when the wearer is upright:
the top portion is vertically above the base portion and the bottom portion is vertically below the base portion;

the first vertical strut is configured such that it can be positioned entirely on a left or right side of the wearer;

the top portion and bottom portion are configured such that they both apply a first force to the left or right side of the wearer;

the flexible belt is configured such that it applies a second force opposite to the first force relative to the wearer; and the first vertical strut is configured such that it can restrict the wearer's motion along a coronal plane.

21. The scoliosis brace of claim 20, further comprising a second vertical strut configured such that it can be positioned entirely on a second side of the wearer opposite the left or right side when the brace is worn by the wearer.

22. The scoliosis brace of claim 20, wherein the brace is further configured such that it can restrict the wearer's motion along at least one of a sagittal plane and a transverse plane when the brace is worn.

23. The scoliosis brace of claim 20, wherein the flexible belt substantially maintains a vertical position of the top portion and the bottom portion when the scoliosis brace is worn by the wearer.

24. The scoliosis brace of claim 20, further comprising a first tension strap that extends from the first vertical strut to the flexible belt at a position anterior to the first vertical strut.

25. The scoliosis brace of claim 20, wherein the first vertical strut further comprises a rounded arm configured to wrap around a chest of the wearer when the brace is worn.

26. The scoliosis brace of claim 20, wherein a length of the first vertical strut is adjustable between each of (a) the top portion and the base portion, and (b) the bottom portion and the base portion.

27. The scoliosis brace of claim 20, wherein the top portion includes a first pad, wherein the bottom portion includes a hip pad, and wherein the base portion, the first pad and the hip pad comprise separate pieces of material.

28. The scoliosis brace of claim 20, wherein the first vertical strut further comprises an angle adjustment mechanism configured to allow a user to adjust an angle of the vertical strut between the top portion and the bottom portion, wherein the angle adjustment mechanism comprises a first strut piece and a second strut piece coupled to one another such that the first strut piece is configured to rotate relative to the second strut piece.

29. The scoliosis brace of claim 20, wherein the flexible belt comprises a tightening mechanism including a first cord that sinuously engages cord guide lobes of first and second cord guides, and is configured to shorten a distance between first and second cord guides when pulled in a first direction.

* * * * *